(12) United States Patent
Ishikawa et al.

(10) Patent No.: US 11,443,714 B2
(45) Date of Patent: Sep. 13, 2022

(54) DISPLAY CONTROL DEVICE, DISPLAY CONTROL METHOD, AND DISPLAY CONTROL PROGRAM

(71) Applicant: FUJIFILM Corporation, Tokyo (JP)

(72) Inventors: Shigetoshi Ishikawa, Kanagawa (JP); Keiji Tsubota, Kanagawa (JP); Haruyasu Nakatsugawa, Kanagawa (JP)

(73) Assignee: FUJIFILM Corporation, Tokyo (JP)

(*) Notice: Subject to any disclaimer, the term of this patent is extended or adjusted under 35 U.S.C. 154(b) by 135 days.

(21) Appl. No.: 16/559,599

(22) Filed: Sep. 3, 2019

(65) Prior Publication Data
US 2020/0105222 A1    Apr. 2, 2020

(30) Foreign Application Priority Data

Sep. 27, 2018  (JP) .............................. JP2018-181294

(51) Int. Cl.
*G09G 5/02* (2006.01)
*G06F 3/0482* (2013.01)
*G06F 3/13* (2006.01)

(52) U.S. Cl.
CPC ............ *G09G 5/02* (2013.01); *G06F 3/0482* (2013.01); *G06F 3/13* (2013.01)

(58) Field of Classification Search
CPC .......... G06F 3/13; G06F 3/0482; G06F 19/30; G06F 19/32; G06F 19/321; G06F 19/324; G09G 5/02; G16H 30/00; G16H 30/40; G16H 40/60; G16H 40/63; G16H 15/00; G16H 10/00; G16H 10/60; G16H 10/40; G16H 80/00; G16H 200/60
See application file for complete search history.

(56) References Cited

U.S. PATENT DOCUMENTS

| | | | | |
|---|---|---|---|---|
| 2005/0021245 | A1* | 1/2005 | Furuno .................. | G06Q 10/10 702/33 |
| 2014/0267299 | A1* | 9/2014 | Couse .................... | G16H 15/00 345/440.2 |
| 2016/0048985 | A1* | 2/2016 | Jones ..................... | G06T 11/206 345/593 |
| 2017/0132914 | A1* | 5/2017 | Dannat ................. | G06Q 10/047 |

FOREIGN PATENT DOCUMENTS

| JP | 2009145115 | | 7/2009 |
|---|---|---|---|
| JP | 2009145115 | A * | 7/2009 |

* cited by examiner

*Primary Examiner* — Alexander Eisen
*Assistant Examiner* — Nathaniel P Brittingham
(74) *Attorney, Agent, or Firm* — JCIPRNET

(57) ABSTRACT

A display control device includes: a first control unit that performs control for displaying a bar for plotting an inspection result for each inspection item in a subject with one direction of the bar representing a value of the inspection result, and displaying a mark representing a last inspection result in the bar; and a second control unit that performs control for displaying information representing a predetermined number of inspection results of at least one of the subject individual or the same variety as a variety of the subject individual for a predetermined inspection item along the one direction of the bar with different color or density depending on a frequency of each inspection result.

20 Claims, 13 Drawing Sheets

FIG. 2

| ID | NAME | SEX | AGE | RACE | VARIETY | INSPECTION RESULT INFORMATION ||||||
|---|---|---|---|---|---|---|---|---|---|---|---|
| | | | | | | EXECUTION DATE | MEDICAL EXAMINATION | IN-HOSPITAL | TOTAL PROTEIN | ALBUMIN | ... |
| 12345-1 | KOTARO | MALE | 7 | DOG | SHETLAND SHEEPDOG | 9/25/2017 | Y | Y | 8.0 | 3.1 | ... |
| | | | | | | 3/5/2017 | Y | Y | 6.0 | 2.8 | ... |
| | | | | | | 12/1/2016 | N | Y | ... | ... | ... |
| | | | | | | 12/1/2016 | N | N | ... | ... | ... |
| ... | ... | ... | ... | ... | ... | ... | ... | ... | ... | ... | ... |

FIG. 5

| | | | 9/25/2017 | |
|---|---|---|---|---|
| | PROTEIN | TOTAL PROTEIN | 8.0* | |
| | | ALBUMIN | 3.1 | |
| | | A/G RATIO | 1.11* | |
| | | TOTAL BILIRUBIN | 0.1* | |
| | ENZYME /ISOZYME | AST/GOT | 68* | |
| | | ALT/GPT | 31 | |
| | | ALP | 133* | |
| | | γ-GTP | 2* | |
| | | LIPASE | 14* | |
| | NITROGEN | UREA NITROGEN | 14* | |
| | | CREATININE | 1.2* | |
| | LIPID | TOTAL CHOLESTEROL | 213* | |
| | | NEUTRAL FAT | 41* | |
| | | CALCIUM | 4.2 | |
| | ELECTROLYTE /MINERAL | INORGANIC PHOSPHORUS | 3.1* | |
| | | BLOOD SUGAR | 88* | |
| | | NATRIUM | 149* | |
| | | POTASSIUM | 10.1* | |
| | | CHLORIDE | 109* | |

| | | 9/25/2017 |
|---|---|---|
| BLOOD CELL | NUMBER OF WHITE BLOOD CELLS | 7100 |
| | NUMBER OF RED BLOOD CELLS | 812* |
| | HEMOGLOBIN | 17.6* |
| | PCV (HEMATOCRIT) | 46.0* |
| | MCV | 69.0* |
| | MCH | 22.9* |
| | MCHC | 33.2* |
| | PLATELET | 31.8* |

12345-1 KOTARO MALE SEVEN YEARS OLD DOG (SHETLAND SHEEPDOG)

INSPECTION | MEDICAL EXAMINATION

ENLARGE

PRINT | CLOSE

FIG. 6

| | | 9/25/2017 | |
|---|---|---|---|
| | TOTAL PROTEIN | 8.0* | |
| PROTEIN | ALBUMIN | 3.1* | |
| | A/G RATIO | 1.11* | |
| | TOTAL BILIRUBIN | 0.1* | |
| ENZYME /ISOZYME | AST/GOT | 68* | |
| | ALT/GPT | 31* | |
| | ALP | 133* | |
| | γ-GTP | 2* | |
| | LIPASE | 14* | |
| NITROGEN | UREA NITROGEN | 14* | |
| | CREATININE | 1.2* | |
| LIPID | TOTAL CHOLESTEROL | 213* | |
| | NEUTRAL FAT | 41* | |
| ELECTROLYTE / MINERAL | CALCIUM | 4.2* | |
| | INORGANIC PHOSPHORUS | 3.1* | |
| | BLOOD SUGAR | 88* | |
| | NATRIUM | 149* | |
| | POTASSIUM | 10.1* | |
| | CHLORIDE | 109* | |

| BLOOD CELL | NUMBER OF WHITE BLOOD CELLS | 7100* |
| | NUMBER OF RED BLOOD CELLS | 812* |
| | HEMOGLOBIN | 17.6* |
| | PCV (HEMATOCRIT) | 46.0* |
| | MCV | 69.0* |
| | MCH | 22.9* |
| | MCHC | 33.2 |
| | PLATELET | 31.8* |

FIG. 7

| | | 9/25/2017 | 3/2017 | 10/2016 |
|---|---|---|---|---|
| PROTEIN | TOTAL PROTEIN | 8.0* | 6.8 | 6.8 |
| | ALBUMIN | 3.1* | 2.8 | 2.8 |
| | A/G RATIO | | 1.10 | 1.02 |
| ENZYME /ISOZYME | TOTAL BILIRUBIN | | 0.2 | 0.2 |
| | AST/GOT | 68* | 30 | 40 |
| | ALT/GPT | | 22 | 29 |
| | ALP | | 165 | 155 |
| | γ-GTP | | 6.0 | 5.0 |
| | LIPASE | 14* | 34 | 34 |
| NITROGEN | UREA NITROGEN | 14* | 15 | 16 |
| | CREATININE | 1.2* | 0.5 | 0.5 |
| LIPID | TOTAL CHOLESTEROL | 213* | 198 | 154 |
| | NEUTRAL FAT | | 81 | 99 |
| ELECTROLYTE /MINERAL | CALCIUM | 4.2* | 5.4 | 5.4 |
| | INORGANIC PHOSPHORUS | 3.1* | 2.9 | 3.0 |
| | BLOOD SUGAR | | 100 | 73 |
| | NATRIUM | 14.9* | 140 | 150 |
| | POTASSIUM | 10.1* | 10.3 | 10.2 |
| | CHLORIDE | 109* | 109 | 115 |
| INFLAMMATION | CRP | 1.2 | | |

| | | 9/25/2017 | 3/28/17 | 10/2016 |
|---|---|---|---|---|
| | NUMBER OF WHITE BLOOD CELLS | 7100* | 6253 | 6400 |
| | NUMBER OF RED BLOOD CELLS | 812* | 580 | 594 |
| | HEMOGLOBIN | 17.6* | 17.6 | 16.4 |
| | PCV (HEMATOCRIT) | 46.0* | 48.5 | 45.0 |
| | MCV | 69.0* | 71.1 | 70.8 |
| | MCH | 22.9* | 22.4 | 22.5 |
| | MCHC | 33.2* | 40.2 | 43.2 |
| BLOOD CELL | PLATELET | 31.8* | 38.2 | 37.5 |
| | LY | 23* | | |
| | MO | 2* | | |
| | EO | 7* | | |
| | GR | 36* | | |
| | RDN | 15.4* | | |
| | PCT | 0.25* | | |
| | MPV | 10.0* | | |
| | PDW | 15.2* | | |
| BLOOD CELL | HEMATOCRIT | 39* | | |
| | TP | 7.7* | | |
| | II | 2* | | |

PRINT  CLOSE

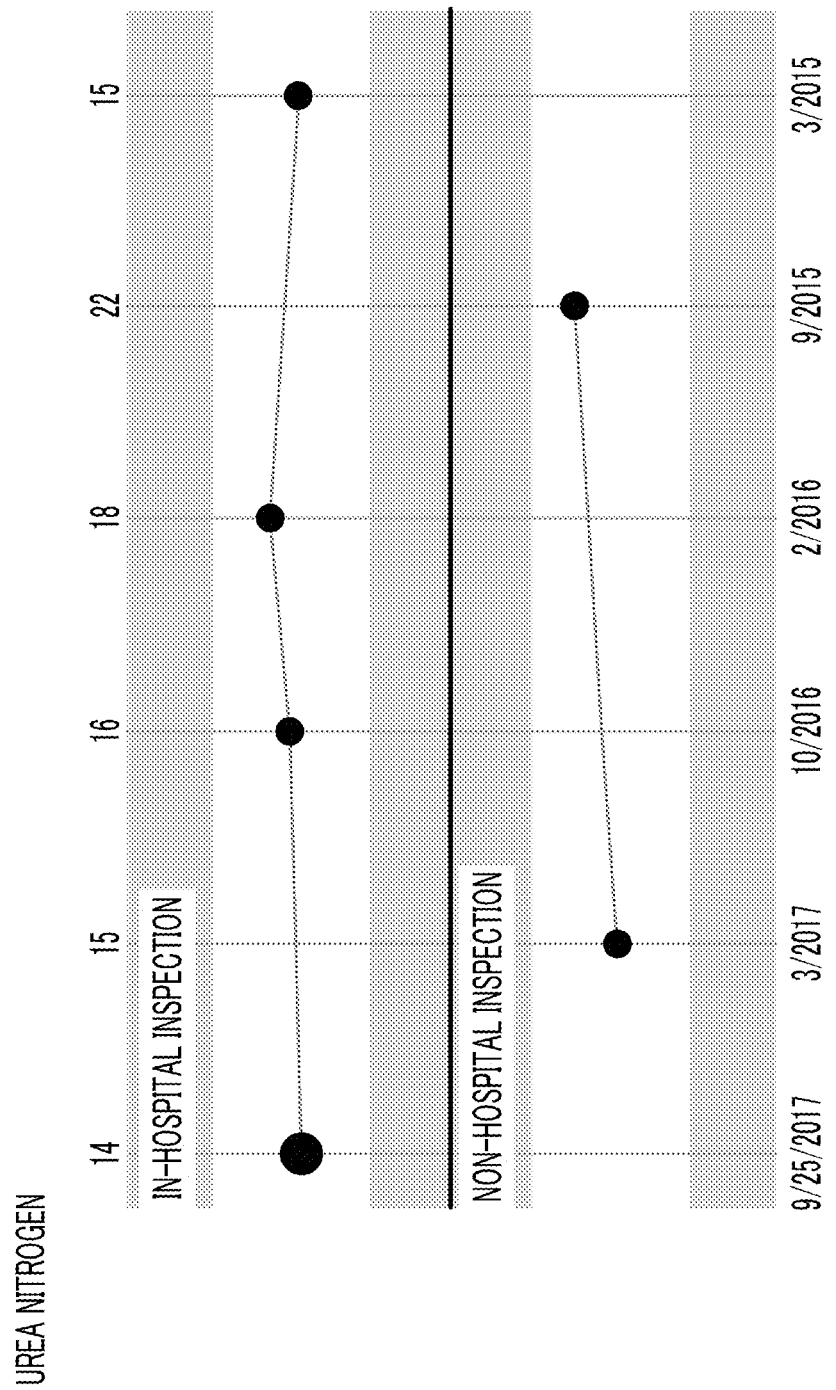

DISPLAY CONTROL DEVICE, DISPLAY CONTROL METHOD, AND DISPLAY CONTROL PROGRAM

CROSS-REFERENCE TO RELATED APPLICATION

This application claims priority from Japanese Patent Application No. 2018-181294, filed on Sep. 27, 2018, the disclosure of which is incorporated by reference herein in their entirety.

BACKGROUND

Field of the Invention

The present disclosure relates to a display control device, a display control method, and a storage medium storing a display control program.

Related Art

A display method that displays a last inspection result and a range of a normal value of an inspection result for each inspection item as information relating to determination of an inspection result of an animal as a subject is disclosed (see Japanese Paten Application Laid-open (JP-A) 2009-145115). In the display method, slide bars representing whether the last inspection result is excessively small, normal, or excessively large with respect to the range of the normal value are displayed in parallel, whereby determination regarding whether or not the last inspection result is normal is easily performed.

However, in the techniques described in JP2009-145115A, for example, in a case where a last inspection result is an abnormal value, it is not possible to determine whether or not the inspection result is abnormal occasionally or whether or not there is a strong tendency that the inspection result is abnormal. Similarly, for example, in a case where the last inspection result is a normal value, it is not possible to determine whether or not the inspection result is normal occasionally or whether or not there is a strong tendency that the inspection result is normal. For this reason, there is a problem in that it is not possible to support appropriate diagnosis of a subject by an examiner, such as a physician.

SUMMARY

The present disclosure has been accomplished in consideration of the above circumstances, and an object of the present disclosure is to provide a display control device, a display control method, and a storage medium storing a display control program capable of supporting appropriate diagnosis of a subject by an examiner.

In order to achieve the above-described object, the present disclosure provides a display control device comprising a first control unit that perforans control for displaying a bar for plotting an inspection result for each inspection item in a subject with one direction of the bar representing a value of the inspection result, and displaying a mark representing a last inspection result in the bar, and a second control unit that perforans control for displaying information representing a predetermined number of inspection results of at least one of the subject individual or the same variety as a variety of the subject individual for a predetermined inspection item along the one direction of the bar with different color or density depending on a frequency of each inspection result.

In the display control device of the present disclosure, in a case where the subject is an animal, the variety may be an animal variety, and in a case where the subject is a human, the variety may be a human race.

In the display control device of the present disclosure, in a case of performing control for displaying information representing the predetermined number of inspection results of the subject individual, the second control unit may perform control for displaying information representing a previous inspection result before the last inspection result displayed under the control of the first control unit.

In the display control device of the present disclosure, in a case of performing control for displaying information representing the predetermined number of inspection results of the same variety as the variety of the subject individual, the second control unit may perform control for displaying information representing all inspection results to be acquired from a storage device storing the inspection results of the same variety or a part of last inspection results among all the inspection results.

In the display control device of the present disclosure, the second control unit may perform control for displaying information representing the predetermined number of inspection results of both of the subject individual and the same variety as the variety of the subject individual.

In the display control device of the present disclosure, the second control unit may perform control for displaying information representing one inspection result by one point.

In the display control device of the present disclosure, in a case where there are a plurality of inspection results having the same value, the second control unit may perform control for displaying information representing the inspection results having the same value on different axes along the one direction.

In the display control device of the present disclosure, the second control unit may perform control for displaying information representing the predetermined number of inspection results by a histogram.

In the display control device of the present disclosure, the second control unit may perform the control by weighting a frequency of an inspection result using a smaller weight value when the inspection result is older.

In the display control device of the present disclosure, the second control unit may perform control for displaying information representing the predetermined number of inspection results by changing a display state depending on at least one of the number of inspections results of the predetermined number of inspection results or a proportion of inspection results before a predetermined point of time in the predetermined number of inspection results.

In the display control device of the present disclosure, the second control unit may perform control for displaying information representing the predetermined number of inspection results by changing color depending on at least one of the number of inspection results of the predetermined number of inspection results or the proportion of inspection results before the predetermined point of time in the predetermined number of inspection results.

In the display control device of the present disclosure, the first control unit may perform control for displaying the mark by changing color or density between a case where the last inspection result is an abnormal value and a case where the last inspection result is a normal value.

The display control device of the present disclosure may further comprise a reception unit that receives the inspection item selected by an examiner, and the predetermined inspection item may be the inspection item received by the reception unit.

The display control device of the present disclosure may further comprise a determination unit that determines whether or not an inspection result is an abnormal value for each inspection item, and the predetermined inspection item may be an inspection item for which an inspection result is determined to be an abnormal value by the determination unit.

The display control device of the present disclosure may further comprise a reception unit that receives the inspection item selected by an examiner, and a third control unit that performs control for displaying a graph representing a history of inspection results including a last inspection result of the subject individual and a predetermined number of previous inspection results from the last inspection result for the inspection item received by the reception unit.

In order to achieve the above-described object, the present disclosure provides a display control method of executing processing, with a computer, for performing control for displaying a bar for plotting an inspection result for each inspection item in a subject with one direction of the bar representing a value of the inspection result, and displaying a mark representing a last inspection result in the bar, and performing control for displaying information representing a predetermined number of inspection results of at least one of the subject individual or the same variety as a variety of the subject individual for a predetermined inspection item along the one direction of the bar with different color or density depending on a frequency of each inspection result.

In order to achieve the above-described object, the present disclosure provides a display control program causing a computer to execute processing for performing control for displaying a bar for plotting an inspection result for each inspection item in a subject with one direction of the bar representing a value of the inspection result, and displaying a mark representing a last inspection result in the bar, and performing control for displaying information representing a predetermined number of inspection results of at least one of the subject individual or the same variety as a variety of the subject individual for a predetermined inspection item along the one direction of the bar with different color or density depending on a frequency of each inspection result.

In order to achieve the above-described object, the present disclosure provides a display control device comprising a first control unit that performs control for displaying a bar for plotting an inspection result for each inspection item in a subject with one direction of the bar representing a value of the inspection result, and displaying a mark representing a last inspection result in the bar, and a second control unit that performs control for displaying information representing a predetermined number of inspection results of at least one of the subject individual or the same variety as a variety of the subject individual for a predetermined inspection item along the one direction of the bar by a histogram of the same color and density.

In order to achieve the above-described object, the present disclosure provides a display control method of executing processing, with a computer, for performing control for displaying a bar for plotting an inspection result for each inspection item in a subject with one direction of the bar representing a value of the inspection result, and displaying a mark representing a last inspection result in the bar, and performing control for displaying information representing a predetermined number of inspection results of at least one of the subject individual or the same variety as a variety of the subject individual for a predetermined inspection item along the one direction of the bar by a histogram of the same color and density.

In order to achieve the above-described object, the present disclosure provides a display control program causing a computer to execute processing for performing control for displaying a bar for plotting an inspection result for each inspection item in a subject with one direction of the bar representing a value of the inspection result, and displaying a mark representing a last inspection result in the bar, and performing control for displaying information representing a predetermined number of inspection results of at least one of the subject individual or the same variety as a variety of the subject individual for a predetermined inspection item along the one direction of the bar by a histogram of the same color and density.

The present disclosure provides a display control device comprising a memory configured to store a command to be executed on a computer, and a processor configured to execute the stored command. The processor performs control for displaying a bar for plotting an inspection result for each inspection item in a subject with one direction of the bar representing a value of the inspection result, and displaying a mark representing a last inspection result in the bar, and performs control for displaying information representing a predetermined number of inspection results of at least one of the subject individual or the same variety as a variety of the subject individual for a predetermined inspection item along the one direction of the bar with different color or density depending on a frequency of each inspection result.

The present disclosure provides a display control device comprising a memory configured to store a command to be executed on a computer, and a processor configured to execute the stored command. The processor performs control for displaying a bar for plotting an inspection result for each inspection item in a subject with one direction of the bar representing a value of the inspection result, and displaying a mark representing a last inspection result in the bar, and performs control for displaying information representing a predetermined number of inspection results of at least one of the subject individual or the same variety as a variety of the subject individual for a predetermined inspection item along the one direction of the bar by a histogram of the same color and density.

According to the present disclosure, it is possible to support appropriate diagnosis of a subject by an examiner.

BRIEF DESCRIPTION OF THE DRAWINGS

FIG. 2 is a diagram showing an example of an inspection result table according to the embodiment.

FIG. 5 is a diagram showing an example of a first display screen according to the embodiment.

FIG. 6 is a diagram showing an example of the first display screen according to the embodiment.

FIG. 7 is a diagram showing an example of a second display screen according to the embodiment.

FIG. 8 is a diagram showing an example of a second display screen according to a modification example.

FIG. 9 is a diagram showing an example of the second display screen according to the embodiment.

FIG. 19 is a diagram showing an example of a graph representing a history of inspection results according to a modification example.

DETAILED DESCRIPTION

Hereinafter, an embodiment for carrying out the technique of the present disclosure will be described in detail referring to the accompanying drawings.

Figure 1:
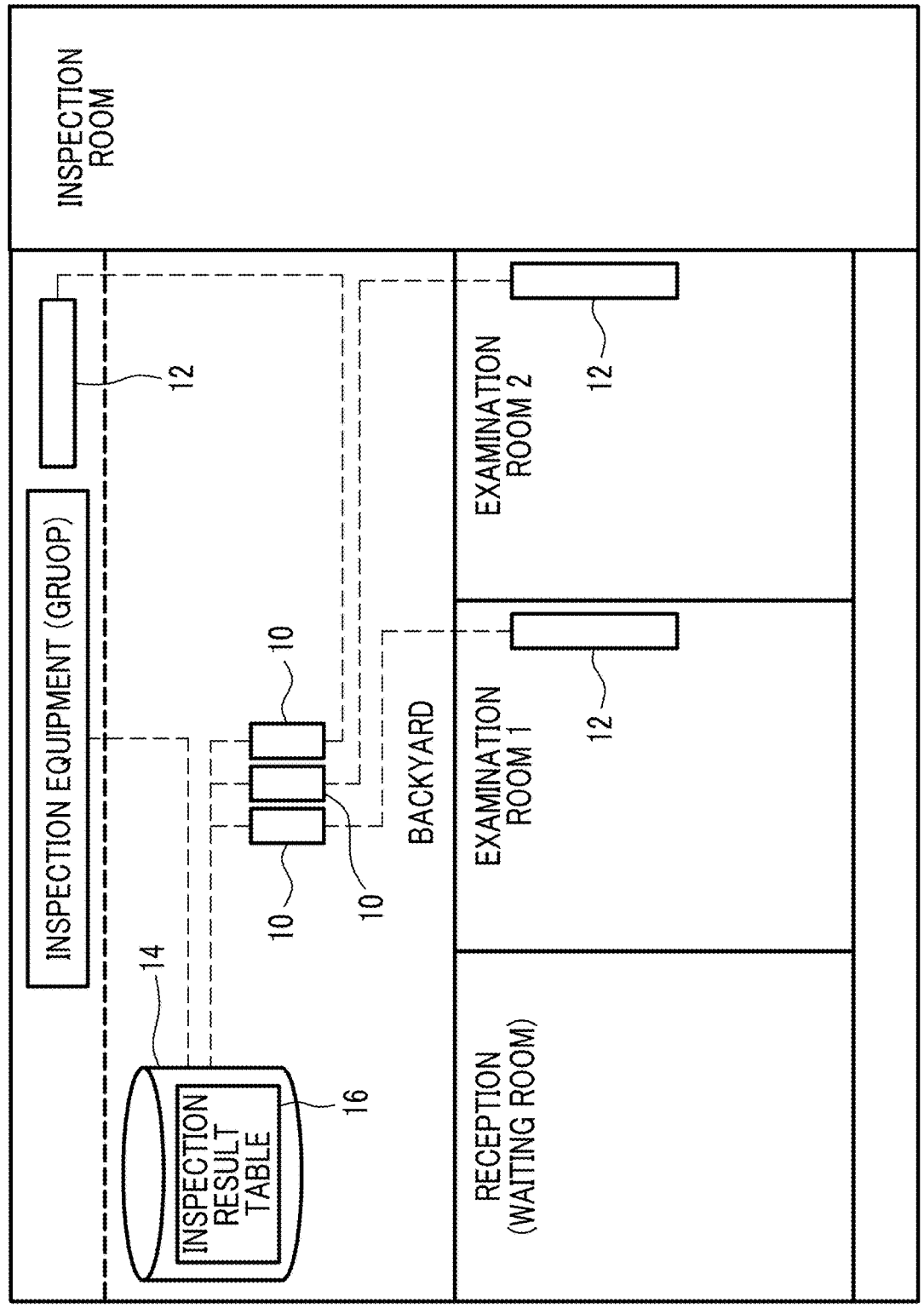
FIG. 1 is a plan view showing an example of an arrangement location of a display control device according to an embodiment.

First, an arrangement location of display control devices 10 according to the embodiment will be described referring to FIG. 1. As shown in FIG. 1, the display control devices 10 are provided in a backyard to correspond to examination rooms of an animal hospital and display devices 12 provided in the backyard. Each display device 12 is connected to the corresponding display control device 10, and the display of the display device 12 is controlled by the display control device 10. As an example of each display control device 10, a personal computer is exemplified, and as an example of each display device 12, a liquid crystal display is exemplified. The display devices 12 are provided in the examination room for explanation to an owner of a subject animal and in the backyard for pre-confirmation of an inspection result.

A storage device 14 as an example of a storage device that stores an inspection result table 16 is provided in the backyard. Each display control device 10 and the storage device 14 are connected to perform communication with each other. The storage device 14 may be, for example, a cloud server that performs communication through a network, such as the Internet. Inspection result data obtained through an inspection with inspection equipment is transferred from the inspection equipment to the storage device 14 through the network. As an example of the inspection equipment, a biochemical inspection machine that inspects protein, enzyme, nitrogen, electrolyte, and the like is exemplified in a case of blood inspection. As an example of the inspection equipment, an immunological inspection machine that inspects immunity or the like, a hemocyte counter that inspects hemocytes, or the like is exemplified. In an inspection room, inspections may be performed by an X-ray image diagnostic apparatus, an ultrasound diagnostic apparatus, an endoscope, and the like, and information of images and the like may be transferred from these apparatuses to the storage device 14 through the network.

FIG. 2 shows an example of the inspection result table 16. As shown in FIG. 2, in the inspection result table 16, an identifier (ID) as an example of identification information, a name, a sex, an age, a race, a variety, and inspection result information are stored for each subject animal. In the inspection result information, an execution date of an inspection, information representing whether or not an inspection is a medical examination (in FIG. 2, denoted as "medical examination") are stored. In the example of FIG. 2, an inspection result where a medical examination column is "Y" represents an inspection result corresponding to an inspection item in a medical examination, and an inspection result where a medical examination column is "N" represents an inspection result corresponding to a temporary inspection including inspection items different from the inspection items in the medical examination.

The temporary inspection used herein means an inspection different from a medical examination to be performed regularly, and for example, an inspection that is performed for diagnosis of a specific disease as a result of an examination of an examiner, such as a veterinarian, is exemplified. The inspection items in the temporary inspection may include the inspection items in the medical examination.

In the inspection result information, information (in FIG. 2, denoted as "in-hospital") representing whether an inspection is performed with inspection equipment provided in an animal hospital or is performed in a facility other than the animal hospital is also stored. Hereinafter, an inspection that is performed with the inspection equipment provided in the animal facility is referred to as an "in-hospital inspection", and an inspection that is performed in a facility other than the animal hospital is referred to as a "non-hospital inspection". In the example of FIG. 2, an inspection result where an in-hospital column is "Y" represents an inspection result obtained by the in-hospital inspection, and an inspection result where the in-hospital column is "N" represents an inspection result obtained by the non-hospital inspection. In the inspection result information, an inspection result (measurement value) of each inspection item obtained by an inspection with the inspection equipment is also stored.

Figure 3:
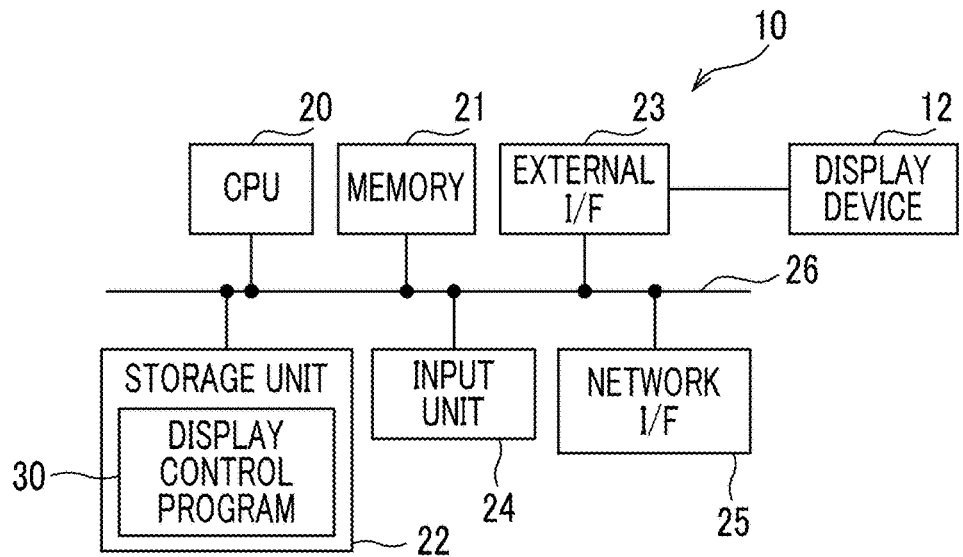
FIG. 3 is a block diagram showing an example of the hardware configuration of the display control device according to the embodiment.

Next, the hardware configuration of the display control device 10 according to the embodiment will be described referring to FIG. 3. As shown in FIG. 3, the display control device 10 includes a central processing unit (CPU) 20, a memory 21 as a temporary storage area, and a nonvolatile storage unit 22. The display control device 10 includes an external interface (I/F) 23 to which the display device 12 is connected, an input unit 24, such as a keyboard and a mouse, and a network I/F 25 that is connected to the network. The CPU 20, the memory 21, the storage unit 22, the external I/F 23, the input unit 24, and the network I/F 25 are connected to a bus 26. The display device 12 has a display unit integrated with a touch panel, and an input of a user on the display device 12 is input to the display control device 10 through the external I/F 23.

The storage unit 22 is implemented by a hard disk drive (HDD), a solid state drive (SSD), a flash memory, or the like. In the storage unit 22 as a storage medium, a display control program 30 is stored. The CPU 20 reads the display control program 30 from the storage unit 22, then, develops the display control program 30 to the memory 21, and executes the developed display control program 30.

Figure 4:
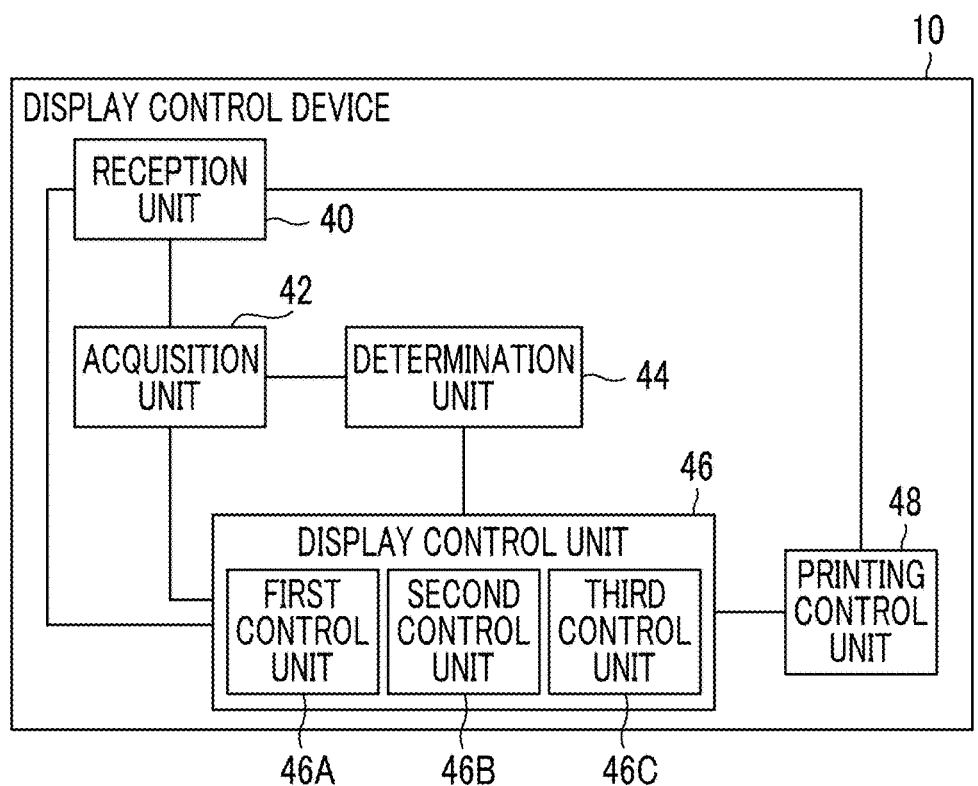
FIG. 4 is a block diagram showing an example of the functional configuration of the display control device according to the embodiment.

Next, the functional configuration of the display control device 10 according to the embodiment will be described referring to FIG. 4. As shown in FIG. 4, the display control device 10 includes a reception unit 40, an acquisition unit 42, a determination unit 44, a display control unit 46, and a printing control unit 48. The display control unit 46 includes a first control unit 46A, a second control unit 46B, and a third control unit 46C. The CPU 20 executes the display control program 30, thereby functioning as the reception unit 40, the acquisition unit 42, the determination unit 44, the display control unit 46, and the printing control unit 48.

The reception unit 40 receives a display instruction of a first display screen on which the inspection result of the medical examination input by the examiner is displayed. The reception unit 40 receives a display instruction of a second display screen on which the inspection result of the temporary inspection input by the examiner is displayed. In the display instructions, an ID of an animal for which an inspection result is to be displayed is included. The reception unit 40 receives a printing instruction input by the examiner. The reception unit 40 receives an inspection item selected by the examiner.

The acquisition unit 42 refers to the inspection result table 16 and acquires the name, the sex, the age, the race, the variety, and the inspection result information corresponding to the ID received by the reception unit 40.

The determination unit 44 determines whether or not the inspection result is an abnormal value for each inspection item included in the inspection result information acquired by the acquisition unit 42. Specifically, the determination unit 44 determines that the inspection result is a normal value in a case where the inspection result is equal to or greater than a lower limit value of the normal value and equal to or less than an upper limit value of the normal value determined in advance for each animal race and each inspection item. The determination unit 44 determines that the inspection result is an abnormal value in a case where the inspection result is less than the lower limit value of the normal value or exceeds the upper limit value of the normal value. In the following description, a range of equal to or greater than the lower limit value of the normal value and equal to or less than the upper limit value of the normal value is referred to as a "normal value range", and a range of less than the lower limit value of the normal value and a range exceeding the upper limit value of the normal value are referred to as an "abnormal value range". The lower limit value and the upper limit value of the normal value may be determined in advance for each animal variety and each inspection item.

The first control unit 46A performs control for switching between the first display screen and the second display screen in response to the display instruction received by the reception unit 40. On each display screen, the first control unit 46A performs control for displaying a bar for plotting an inspection result for each inspection item in a subject on the display device 12 with one direction of the bar representing a value of the inspection result, and displaying a mark representing a last inspection result in the bar. During the control, the first control unit 46A performs control for displaying the mark by changing color between a case where the last inspection result is an abnormal value and a case where the last inspection result is a normal value. For the inspection items for which the last inspection result is an abnormal value, the first control unit 46A performs control for displaying the mark by changing color between a case where the inspection result is less than the lower limit value of the normal value and a case where the inspection result exceeds the upper limit value of the normal value. The first control unit 46A may perform control for displaying the mark by changing density between a case where the last inspection result is an abnormal value and a case where the last inspection result is a normal value.

In performing control for displaying the bar, the first control unit 46A performs control for displaying the normal value range and the abnormal value range to be visually recognizable. In performing control for displaying the bar, the first control unit 46A performs control for displaying the last inspection result to be distinguishable whether the last inspection result is a result obtained by the in-hospital inspection or a result obtained by the non-hospital inspection.

On each display screen, the second control unit 46B performs control for displaying information representing a predetermined number of inspection results of the subject individual for a predetermined inspection item along the one direction of the bar with different density depending on a frequency of each inspection result. In the embodiment, the second control unit 46B performs the control for all of the last inspection items as the predetermined inspection item. In addition, during the control, the second control unit 46B performs control for displaying information representing a predetermined number of previous inspection results before the last inspection result displayed under the control of the first control unit 46A. Specifically, during the control, the second control unit 46B uses all previous inspection results before the last inspection result stored in the inspection result table 16 as the predetermined number of inspection results.

The second control unit 46B performs control for displaying information representing one inspection result by one rectangular point. That is, when the frequency of the inspection result is higher, many points are displayed in an overlapped manner and density becomes higher. A shape of a point representing one inspection result is not particularly limited, and may be a shape, such as a circular shape, other than the rectangular shape.

On each display screen, in a case where an inspection item is selected by the examiner, the third control unit 46C performs control for displaying the following graph for the selected item received by the reception unit 40. That is, in this case, the third control unit 46C performs control for displaying a graph representing a history of inspection results including a last inspection result of the subject individual and a predetermined number of previous inspection results from the last inspection result. The third control unit 46C may perform control for displaying any one of the normal value range and the abnormal value range to be visually recognizable in the graph.

The third control unit 46C sets the number of previous inspection results displayed as a graph on the first display screen to be greater than the number of previous inspection results displayed as a graph on the second display screen.

The third control unit 46C performs control for displaying, on the display device 12, a graph including the inspection result of the medical examination as a history of the inspection results for the inspection items included in the medical examination among the inspection items in the temporary inspection on the second display screen.

In a case where the printing instruction is received by the reception unit 40, the printing control unit 48 performs control such that a printing apparatus (not shown) lays out and prints a screen to be displayed on the display device 12 to fit onto one sheet. It is desirable that printing is performed in color. In a case where a printed display result is viewed later, an inspection item having an abnormal value may be described in a sentence to be easily found (for example, "a blood glucose level and AST/GOT exceed upper limits" or the like). Alternatively, an inspection item for which an inspection result is an abnormal value may be highlighted by changing a font to a boldfaced type, underlining letters, or changing the font to another font (for example, from Gothic to italics, or the like). Even in a case where the printing apparatus is a black-white machine, an inspection item for which an inspection result is an abnormal value may be highlighted by changing a font to a boldfaced type such that the inspection item for which the inspection result is an abnormal value is easily discriminated. In this case, an inspection item for which an inspection result is an abnormal value may be highlighted by underlining letters, changing a font to another font, increasing a font size to be greater than an inspection item for which an inspection result is a normal value, filling in color with white letters (for example, letters are white and the periphery is black), or the like.

FIG. 5 shows an example of a first display screen. As shown in FIG. 5, the first display screen according to the embodiment includes display areas 60, 62, and 64. The display area 60 is a header portion, and the ID, the name, the sex, the age, the race, and the variety of the subject animal are displayed in the display area 60.

In the display area 64, a list of last inspection results is displayed under the control of the first control unit 46A and the second control unit 46B. As shown in FIG. 5, in the list of inspection results, a value of the inspection result and a bar 70 for plotting the inspection result for each inspection item are displayed, and a mark 71 representing a last inspection result is displayed in the bar 70. In the bar 70, one direction (in the example of FIG. 5, a lateral direction in a front view) represents the value of the inspection result. In FIG. 5, although a rectangular shape is applied as the shape of the bar 70, the shape of the bar 70 is not particularly limited, and for example, a shape, such as an elliptical shape, other than the rectangular shape may be applied as the shape of the bar 70. In FIG. 5, although a circular shape is applied as the shape of the mark 71, the shape of the mark 71 is not particularly limited, and for example, a shape, such as a rectangular shape, other than the circular shape may be applied as the shape of the mark 71.

The color of the mark 71 is different depending on the inspection result. In the embodiment, the color of the mark 71 is made black in a case where the inspection result is a normal value. The color of the mark 71 is made blue in a case where the inspection result is an abnormal value and is less than the lower limit value of the normal value, and is made red in a case where the inspection result is an abnormal value and exceeds the upper limit value of the normal value. A color combination of the mark 71 is not limited to the above-described example. The color of the mark 71 may be the same color uniformly.

In the bar 70, for example, the normal value range is shaded in white, such that the normal value range and the abnormal value range are displayed to be visually recognizable. Below the bar 70 in a front view, the lower limit value and the upper limit value of the normal value are displayed. In a case where the inspection result is a result obtained by the non-hospital inspection, a mark 72 representing the inspection result obtained by the non-hospital inspection is displayed on an upper right side of the value of the inspection result in a front view. In a case where the inspection result is a result obtained by the in-hospital inspection, the mark 72 is not displayed on the upper right side of the value of the inspection result in a front view. Accordingly, it is possible to distinguish whether the inspection result is a result obtained by the in-hospital inspection or a result obtained by the non-hospital inspection based on the presence or absence of the mark 72.

Below the bar 70 in a front view, information 73 representing a predetermined number of previous inspection results before the last inspection result is displayed with different density depending on the frequency of each inspection result under the control of the second control unit 46B. In the embodiment, one previous inspection result is plotted by one rectangular point at a position along the one direction of the bar 70 corresponding to the value of the inspection result. Accordingly, when the frequency is higher, the points overlap and the density becomes higher, and the information 73 is displayed in a rectangular shape having gradation depending on the frequency. Information 73 may be displayed above the bar 70 in a front view. Information 73 may be displayed in an area (that is, on the bar 70) inside the bar 70.

The examiner confirms information displayed in the display area 64 and performs an operation to select an inspection item to be focused through the input unit 24 or the display device 12. As the selection operation, an operation (for example, single-click) to designate an inspection result once, an operation (for example, double-click) to designate the inspection result successively twice, or the like is exemplified. In a case where the reception unit 40 receives the inspection item selected by the examiner with the selection operation, as shown in FIG. 6, a graph relating to the selected inspection item is displayed in the display area 62 under the control of the third control unit 46C.

As shown in FIG. 6, a check mark 74 representing that the inspection item is selected is displayed on a left side of the inspection item selected by the examiner in a front view in the display area 64. FIG. 6 shows an example where four inspection items of "total protein", "AST/GOT", "lipase", and "urea nitrogen" are selected.

As shown in FIG. 6, in the display area 62, a graph representing a history of inspection results including a last inspection result of the subject individual for the selected inspection item and a predetermined number of previous inspection results from the last inspection result is displayed. In the embodiment, a graph representing a history of six inspection results in total including the last inspection result and five previous inspection results before the last inspection result is displayed. The vertical axis of the graph shown in FIG. 6 is the first axis representing the inspection result, and the horizontal axis is the second axis representing the time series. For example, in regard to a background color the display area of the graph, the normal value range is made white and the abnormal value range is made gray, whereby the normal value range and the abnormal value range can be visually recognized. In regards to the colors of the points plotted in the graph, similarly to the colors of the marks 71, a point corresponding to the abnormal value less than the lower limit value of the normal value is made blue, a point corresponding to the abnormal value exceeding the upper limit value of the normal value is made red, and a point corresponding to the normal value is made black.

A display order of the graphs in the display area 62 is not particularly limited. For example, the graphs may be displayed from above in a front view in an order selected by the examiner, or the graphs may be displayed with priority (for example, at an upper position in a front view) in a descending order of a degree of abnormality of the inspection result. In this case, a form in which the degree of abnormality is the ratio of an absolute value of the difference between the inspection result and the lower limit value to the lower limit value in a case where the inspection result is less than the lower limit value of the normal value, and is the ratio of an absolute value of the difference between the inspection result and the upper limit value to the upper limit value in a case where the inspection result exceeds the upper limit value of the normal value is exemplified. In this case, a form in which the degree of abnormality is higher when the ratio is greater is exemplified. The degree of abnormality may be derived by an artificial intelligence (AI) technique. As the AI in this case, a form in which a deep neural network with a history of inspection results for an inspection item, for which the inspection result is an abnormal value, as input and the degree of abnormality as output is applied is exemplified.

In an upper portion of the display area 62, an inspection button and a medical examination button are displayed, and in a state in which the first display screen is displayed, the examiner designates the inspection button, such that the first display screen can be switched to the second display screen. Similarly, in a state in which the second display screen described below is displayed, the examiner designates the medical examination button, such that the second display screen can be switched to the first display screen.

FIG. 7 shows an example of a second display screen. As shown in FIG. 7, similarly to the first display screen, the second display screen according to the embodiment includes display areas 60, 62, and 64. Hereinafter, only portions on the second display screen different from the first display screen will be described.

As shown in FIG. 7, on the second display screen, for each of the inspection items included in the medical examination among the inspection items in the last temporary inspection, the inspection result of the medical examination is displayed as the history of the inspection results in the list of inspection results of the display area 64. In the list of inspection results of the display area 64 on the second display screen, for each of the inspection items (in the example of FIG. 7, "A/G ratio" and the like) that are not included in the last temporary inspection and are included in a previous medical examination, the inspection result of the last temporary inspection is not displayed.

Figure 8:
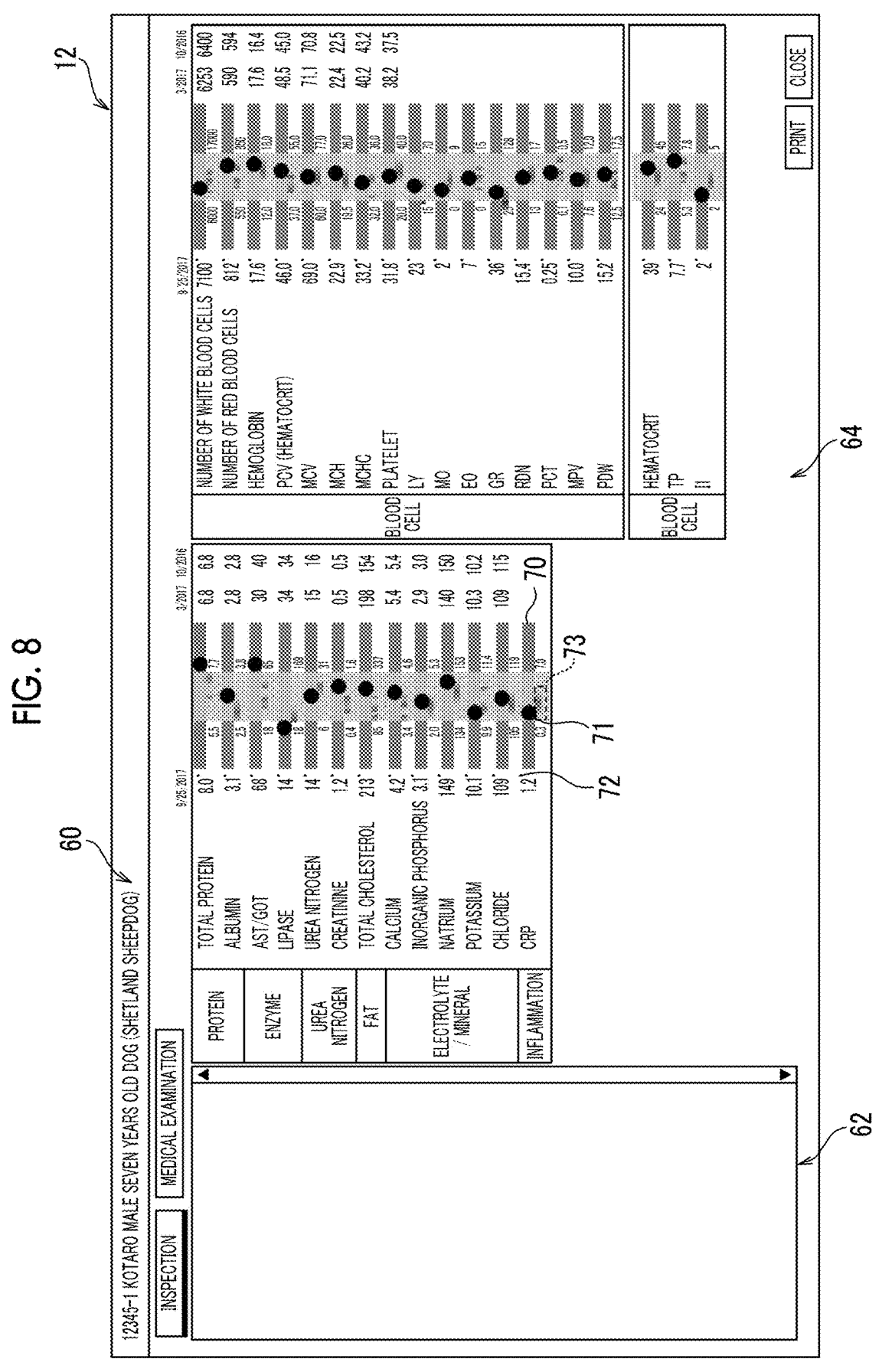

As an example, as shown in FIG. 8, in the list of inspection results of the display area 64 on the second display screen, for each of the inspection items (for example, "A/G ratio" and the like shown in FIG. 7) that are not included in the last temporary inspection and are included in the previous medical examination, the inspection item itself may not be displayed.

Figure 9:
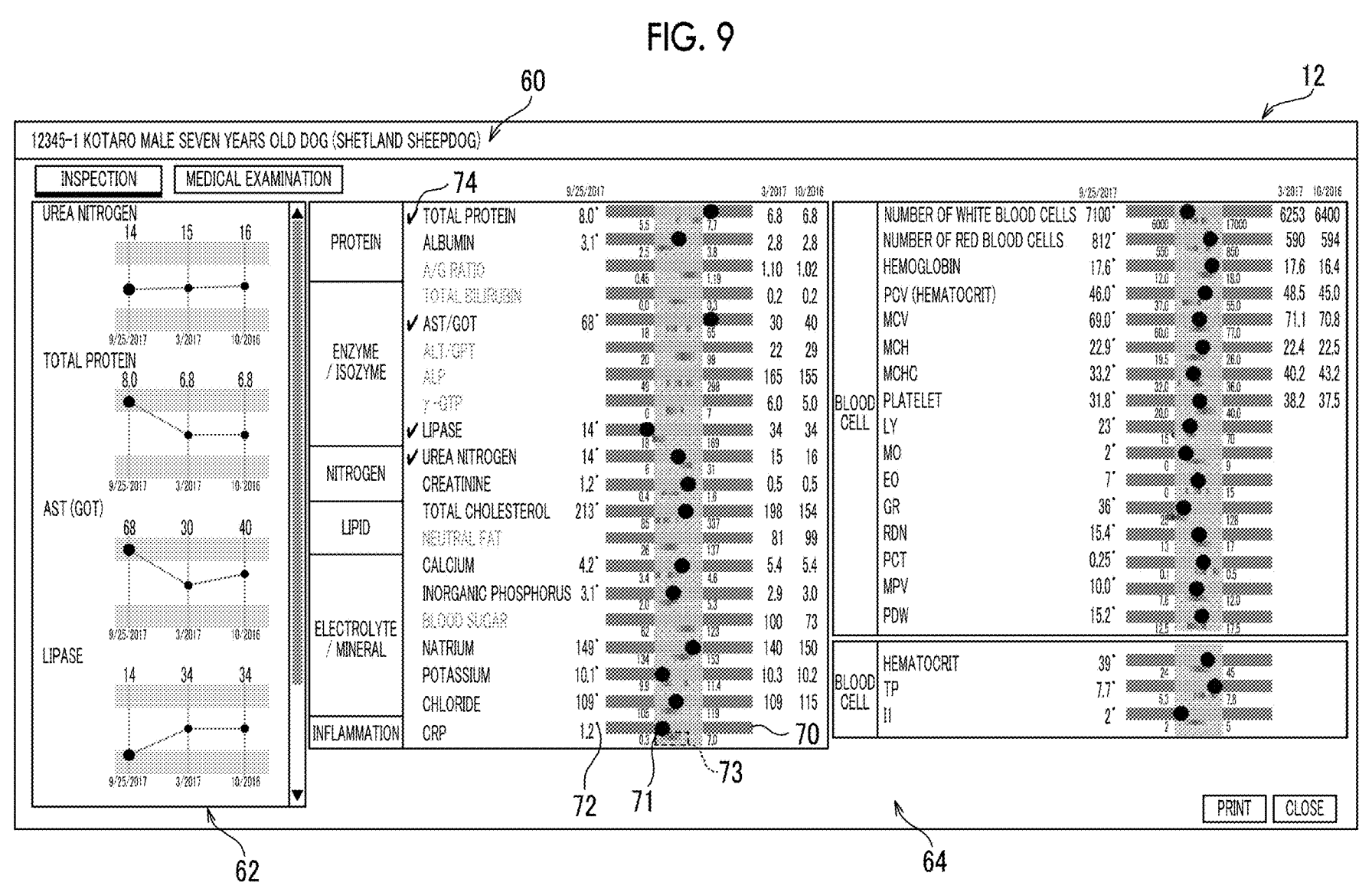

Even on the second display screen, similarly to the first display screen, in a case where the reception unit 40 receives the inspection item selected by the examiner, as shown in FIG. 9, the graph relating to the selected inspection item is displayed in the display area 62 under the control of the third control unit 46C. On the second display screen, the number of inspection results displayed as the history in the graph of the display area 62 is smaller than that on the first display screen. On the second display screen, for each of the inspection items included in the medical examination among the inspection items in a last temporary inspection, the inspection result of the medical examination is included as the history of the inspection results in the graph of the display area 62.

Figure 10:
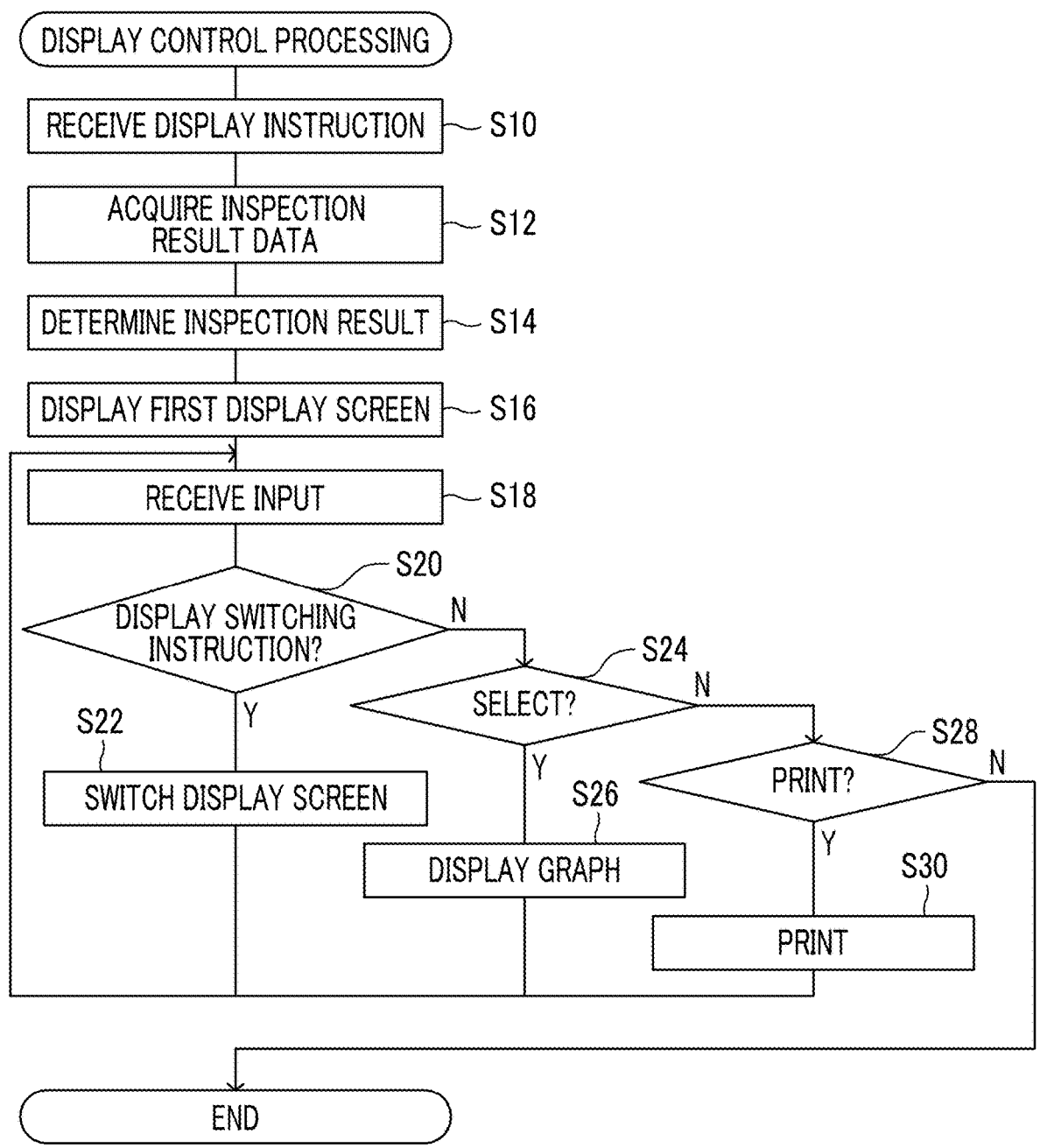
FIG. 10 is a flowchart showing an example of display control processing according to the embodiment.

Next, operation of the display control device 10 according to the embodiment will be described referring to FIG. 10. The CPU 20 executes the display control program 30, whereby display control processing shown in FIG. 10 is executed. The display control processing shown in FIG. 10 is executed, for example, in a case where the display control device 10 receives a display instruction of a screen including an ID of a subject animal input by the examiner.

In Step S10 of FIG. 10, the reception unit 40 receives the display instruction of the screen including the ID of the subject animal input by the examiner. In Step S12, the acquisition unit 42 refers to the inspection result table 16 and acquires the name, the sex, the age, the race, the variety, and the inspection result information corresponding to the ID received through the processing of Step S10.

In Step S14, as described above, the determination unit 44 determines whether or not the inspection result is an abnormal value for each inspection item included in the inspection result information acquired through the processing of Step S12. In Step S16, as described above, the first control unit 46A and the second control unit 46B perform control for displaying the first display screen on the display device 12 based on various kinds of information acquired through the processing of Step S12 and a determination result through the processing of Step S14. During the control, as described above, the first control unit 46A and the second control unit 46B performs control for displaying a list of inspection results of a last medical examination in the display area 64 of the first display screen. In this way, in the embodiment, although the first display screen is displayed on the display device 12 as an initial screen, the second display screen may be displayed as an initial screen. The examiner may select which of the first display screen and the second display screen is displayed as an initial screen.

In Step S18, the reception unit 40 receives an input of the examiner. In Step S20, the first control unit 46A determines whether or not the input received through the processing of Step S18 is a switching instruction between the first display screen and the second display screen. In a case where the determination is negative, the process progresses to Step S24, and in a case where the determination is affirmative, the process progresses to Step S22. Specifically, in a case where the inspection button is designated in a state in which the first display screen is displayed or in a case where the medical examination button is designated in a state in which the second display screen is displayed, the determination of Step S20 is affirmative.

In Step S22, the first control unit 46A and the second control unit 46B perform control for switching between the first display screen and the second display screen according to the input received through the processing of Step S18. Specifically, in a case where the inspection button is designated in a state in which the first display screen is displayed, the first control unit 46A and the second control unit 46B perform control for displaying the second display screen on the display device 12. In a case where the medical examination button is designated in a state in which the second display screen is displayed, the first control unit 46A and the second control unit 46B perform control for displaying the first display screen on the display device 12. In a case where the processing of Step S22 ends, the process returns to Step S18.

In Step S24, the first control unit 46A determines whether or not the input received through the processing of Step S18 is an input corresponding to an operation to select an inspection item. In a case where the determination is negative, the process progresses to Step S28, and in a case where the determination is affirmative, the process progresses to Step S26.

In Step S26, as described above, the third control unit 46C performs control for displaying the graph for the selected inspection item in the display area 62. In a case where the processing of Step S26 ends, the process returns to Step S18.

In Step S28, the first control unit 46A determines whether or not the input received through the processing of Step S18 is an input corresponding to designation of the print button. In a case where the determination is affirmative, the process progresses to Step S30. In Step S30, the printing control unit 48 performs control such that the printing apparatus lays out and prints the screen displayed on the display device 12 to fit onto one sheet as described above. In a case where the processing of Step S30 ends, the process returns to Step S18.

In a case where the determination of Step S28 is negative, the display control processing ends.

As described above, according to the embodiment, the bar 70 with one direction representing the value of the inspection result and the mark 71 representing the last inspection result are displayed for each inspection item. In addition, the information 73 representing the predetermined number of inspection results of the subject individual for the predetermined inspection item is displayed along the one direction with different density depending on the frequency of each inspection result. Accordingly, the examiner can visually recognize the last inspection result and the frequency of the inspection result at one time, and as a result, it is possible to support appropriate diagnosis of the subject by the examiner.

In the above-described embodiment, although a case where the control for displaying the information 73 representing the predetermined number of inspection results of the subject individual along the one direction of the bar 70 with different density depending on the frequency of each inspection result has been described, the present disclosure is not limited thereto. For example, control for displaying the information 73 along the one direction of the bar 70 with different color depending on the frequency of each inspection result may be performed.

In the above-described embodiment, although a case where the information 73 representing the predetermined number of inspection results of the subject individual is displayed has been described, the present disclosure is not limited thereto. For example, a form may be made in which the information 73 representing the predetermined number of inspection results of the same variety as the variety of the subject individual is displayed. In this case, the examiner can ascertain the tendency of the inspection result of the same variety as the variety of the subject individual, instead of the subject individual. In this case, a form in which, as the inspection results used for the display of the information 73, all inspection results of the same variety as the variety of the subject individual to be acquired from the inspection result table 16 or a part (for example, for last one year) of last inspection results are applied is exemplified. Information representing the predetermined number of inspection results of the subject individual and information representing the predetermined number of inspection results of the same variety as the variety of the subject individual may be switched and displayed according to a user's operation.

Figure 11:
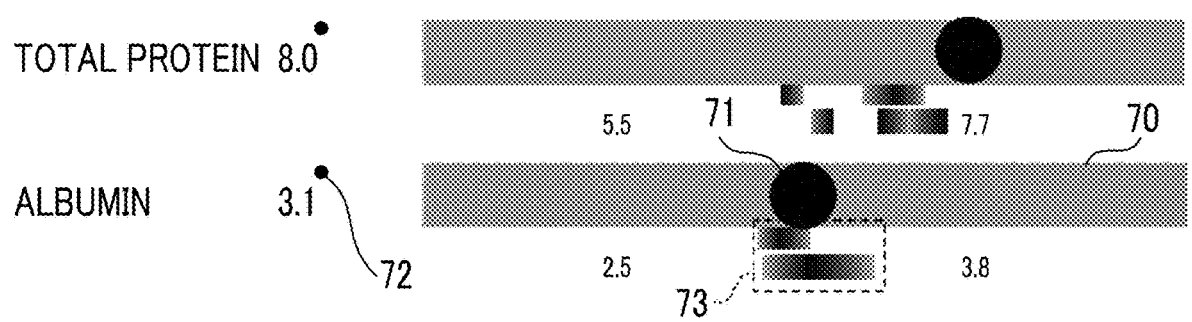
FIG. 11 is an enlarged view in which a part of a display screen according to a modification example is enlarged.

For example, as shown in FIG. 11, a form may be made in which, as the information 73, both of information representing the predetermined number of inspection results of the subject individual and information representing the predetermined number of inspection results of the same variety as the variety of the subject individual are displayed. FIG. 11 shows an example where information representing the predetermined number of inspection results of the subject individual and information representing the predetermined number of inspection results of the same variety as the variety of the subject individual are displayed in parallel vertically below the bar 70 in a front view. For example, information representing the predetermined number of inspection results of the subject individual and information representing the predetermined number of inspection results of the same variety as the variety of the subject individual may be displayed by changing color. For example, information representing the predetermined number of inspection results of the subject individual may be displayed above the bar 70 in a front view, and information representing the predetermined number of inspection results of the same variety as the variety of the subject individual may be displayed below the bar 70 in a front view. FIG. 11 shows a state in which two inspection items among the inspection items in the display area 64 shown in FIGS. 5 to 9 are enlarged. The state is the same as in FIGS. 12 to 18 described below.

Figure 12:
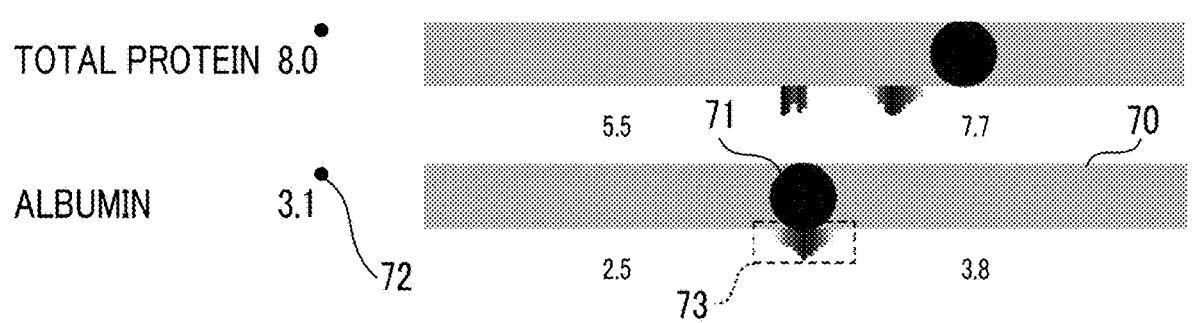
FIG. 12 is an enlarged view in which a part of a display screen according to a modification example is enlarged.
Figure 13:
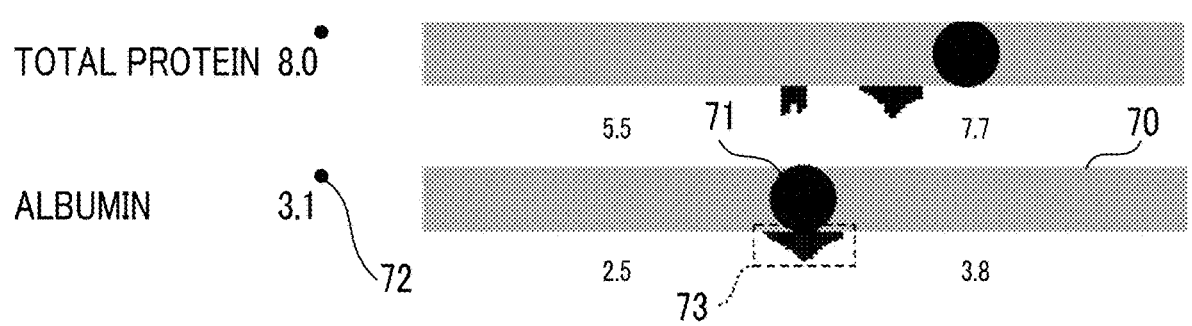
FIG. 13 is an enlarged view in which a part of a display screen according to a modification example is enlarged.

In the above-described embodiment, as shown in FIG. 12, a form may be made in which the information 73 is displayed by a histogram. FIG. 12 shows an example where, when the frequency is higher, the density becomes higher, and rectangular points are extended in a direction (a vertical direction the screen in a front view) perpendicular to one direction of the bar 70 representing the inspection result. For example, as shown in FIG. 13, a form may be made in which the information 73 is displayed along the one direction of the bar 70 by a histogram of the same color and density.

Figure 14:
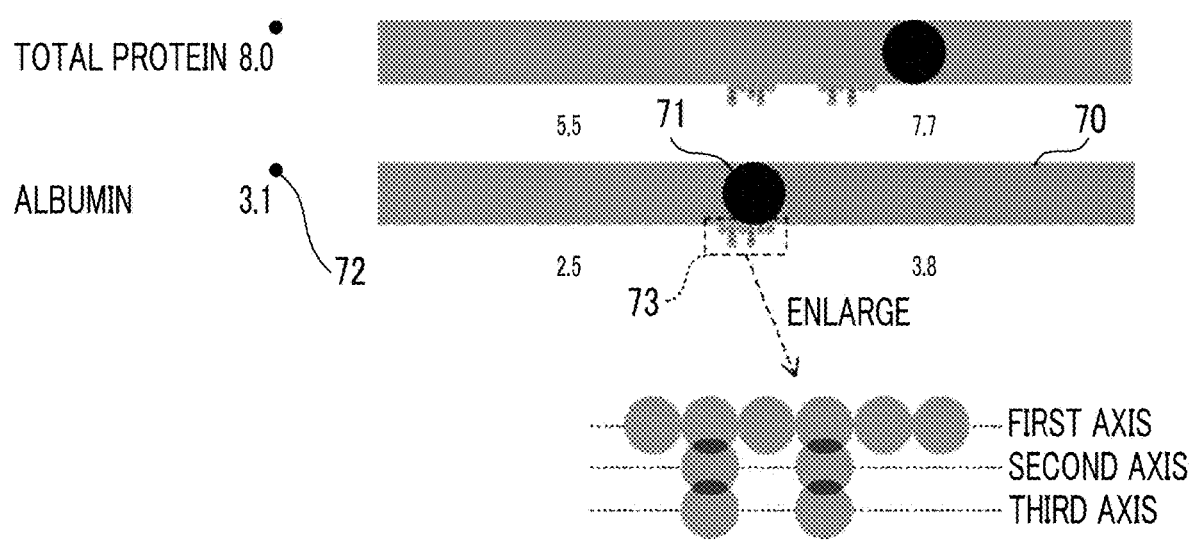
FIG. 14 is an enlarged view in which a part of a display screen according to a modification example is enlarged.

In the above-described embodiment, although a case where information representing the predetermined number of inspection results of the subject individual is displayed on one axis along the one direction of the bar 70 has been described, the present disclosure is not limited thereto. For example, as shown in FIG. 14, a form may be made in which, in a case where a plurality of inspection results having the same value are present, information representing the inspection results having the same value is displayed on different axes along the one direction of the bar 70. FIG. 14 shows an example where a shape of a point representing one inspection result is a circular shape, and the number of axes is three. In this case, as shown in FIG. 14, in displaying information representing the inspection results having the same value by one point on each of different axes, a form in which points are displayed to partially overlap each other is exemplified. In this case, the overlapped portion is displayed with high density.

Figure 15:
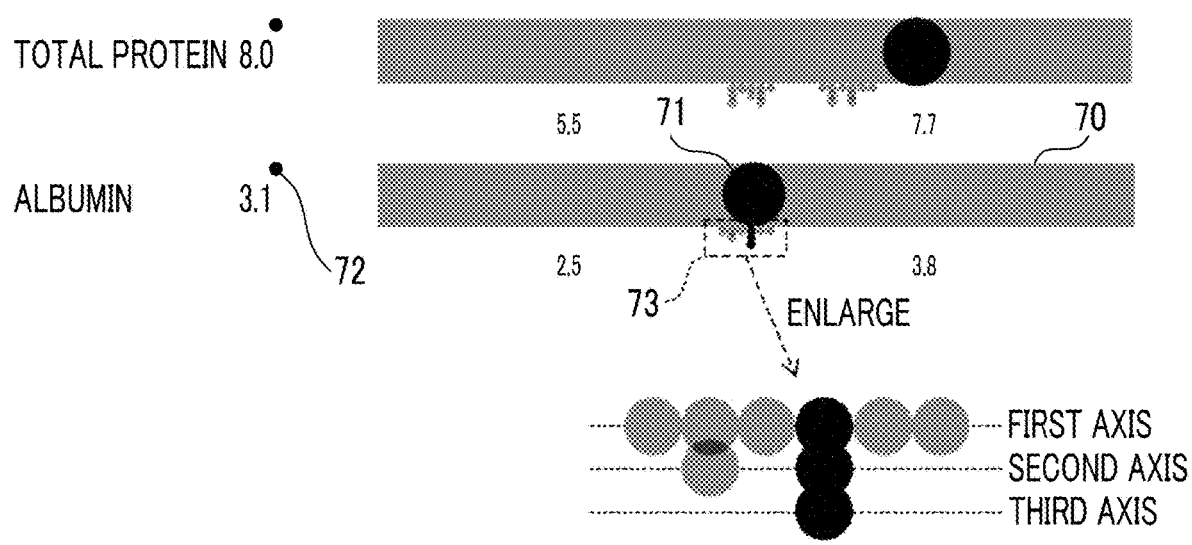
FIG. 15 is an enlarged view in which a part of a display screen according to a modification example is enlarged.

In the form example, as shown in FIG. 15, a form may be made in which an inspection result, the frequency of which exceeds the number of axes, is displayed with color different from an inspection result, the frequency of which is equal to or less than the number of axes. FIG. 15 shows an example where the color of an inspection result, the frequency of which exceeds four, is different.

Figure 16:
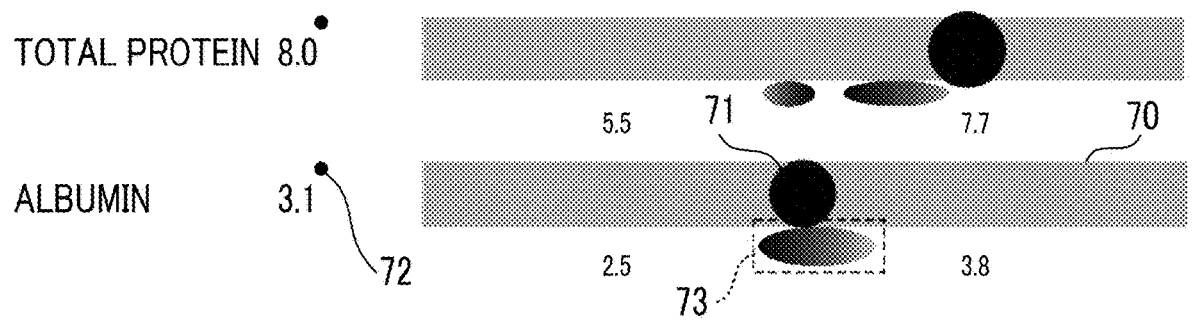
FIG. 16 is an enlarged view in which a part of a display screen according to a modification example is enlarged.
Figure 17:
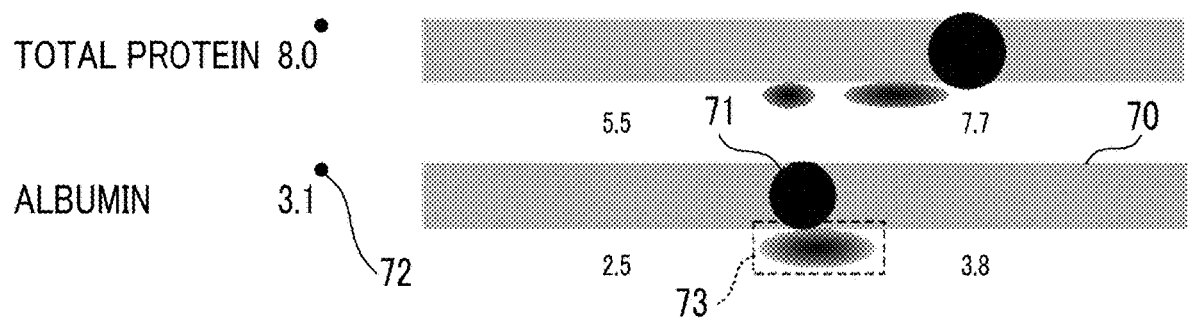
FIG. 17 is an enlarged view in which a part of a display screen according to a modification example is enlarged.

In the above-described embodiment, although a case where a rectangular shape is applied as the shape of the information 73 representing the predetermined number of inspection results of the subject individual has been described, the present disclosure is not limited thereto. For example, as shown in FIG. 16, a form may be made in which an elliptical shape is applied as the shape of the information 73 representing the predetermined number of inspection results of the subject individual. In the form example, as shown in FIG. 17, the density may be lowered with increase of the distance from the center along the direction perpendicular to the direction of the bar 70 representing the inspection result.

In the embodiment, the frequency of the inspection result may be weighted using a smaller weight value when the inspection result is older. In this case, a form in which 1 is used as the weight value of the inspection results for last three years (that is, a single inspection result becomes a frequency of 1), 0.5 is used as the weight value of the inspection results from last three years ago and until last six years (that is, two times of inspection results become a frequency of 1), and 0.25 is used as the weight value of the inspection results before last six years (that is, four times of inspection results become a frequency of 1) is exemplified.

Figure 18:
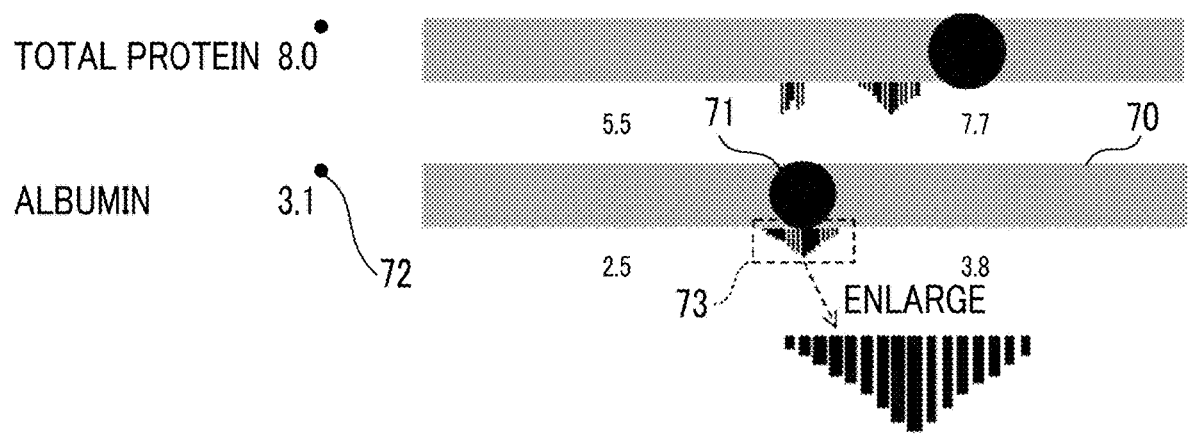
FIG. 18 is an enlarged view in which a part of a display screen according to a modification example is enlarged.

In the above-described embodiment, a form may be made in which a display state of the information 73 representing the predetermined number of inspection results is changed depending on at least one of the number of inspection results of the predetermined number of inspection results of the subject individual or a proportion of inspection results before a predetermined point of time in the number of inspection results of the predetermined number of inspection results. Specifically, for example, in a case where the number of inspection results of the predetermined number of inspection results of the subject individual is equal to or less than a threshold, the information 73 is displayed with color different from in a case where the number of inspection results is equal to or greater than the threshold. For example, in a case where the proportion of the inspection results before the predetermined point of time in the number of inspection results of the predetermined number of inspection results of the subject individual is equal to or less than a threshold, the information 73 is displayed with color different from in a case where the proportion of the inspection results is equal to or greater than the threshold. For example, as shown in FIG. 18, in a case where the predetermined number of inspection results of the subject individual is equal to or less than the threshold value, a histogram is displayed in a discrete manner. In these form examples, it is possible to ascertain the accuracy of the frequency of the inspection result based on at least one of the number of inspection results or the oldness of the inspection result.

In the above-described embodiment, although a case where the information 73 is displayed for all of the last inspection items has been described, the present disclosure is not limited thereto. For example, a form may be made in which the information 73 is displayed for the inspection items selected by the examiner and received by the reception unit 40. For example, a form may be made in which the information 73 is displayed for the inspection items for which the inspection result is determined to be an inspection result by the determination unit 44.

In the above-described embodiment, the graph displayed in the display area 62 may be displayed to be distinguishable whether or not the inspection result is a result obtained by the in-hospital inspection or a result obtained by the non-hospital inspection. In this case, as shown in FIG. 19, a form in which a graph representing a history of inspection results obtained by the in-hospital inspection and a graph representing a history of inspection results obtained by the non-hospital inspection are displayed in parallel vertically in a front view is exemplified. For example, in the graph in the display area 62 shown in FIG. 6, the color of the point to be plotted is changed between the inspection result obtained by the in-hospital inspection and the inspection result obtained by the non-hospital inspection.

In the embodiment, although a case where an animal other than a human is applied as the subject has been described, the present disclosure is not limited thereto. A form may be made in which a human is applied as the subject. In this case, the variety in the embodiment corresponds to a human race. In this case, a form may be made in which information representing a predetermined number of inspection results of the same age as the age of the subject is displayed with different color or density depending on the frequency of each inspection result. In this case, a form may be made in which information representing a predetermined number of inspection results of a relative of the subject is displayed with different color or density depending on the frequency of each inspection result.

In the embodiment, a form may be made in which a scheduled date of a next medical examination is further displayed on at least one of the first display screen or the second display screen. The scheduled date in this case can be obtained, for example, by adding an interval (for example, once half a year) of a medical examination determined in advance for each variety and age to an execution date of a last medical examination.

In the embodiment, a form may be made in which, in a case where the print button is designated, an explanation of an inspection content of an inspection item, for which the inspection result is an abnormal value, and a method (for example, medication, exercise, food, or the like) of improving the inspection result are further printed.

In the embodiment, a form may be made in which, in a case where a graph displayed in the display area 62 is selected and a non-display instruction (for example, a double-tap operation or the like) is input, the selected graph is made to be not displayed.

In the above-described embodiment, as the hardware structures of the processing units that execute various kinds of processing, for example, the reception unit 40, the acquisition unit 42, the determination unit 44, the display control unit 46, and the printing control unit 48, various processors described below can be used. Various processors include a programmable logic device (PLD) that is a processor capable of changing a circuit configuration after manufacture, such as a field programmable gate array (FPGA), a dedicated electric circuit that is a processor having a circuit configuration dedicatedly designed for executing specific processing, such as an application specific integrated circuit (ASIC), and the like, in addition to a central processing unit (CPU) that is a general-purpose processor executing software (program) to function as various processing units, as described above.

One processing unit may be configured of one of various processors described above or may be configured of a combination of two or more processors (for example, a plurality of FPGAs or a combination of a CPU and an FPGA) of the same type or different types. A plurality of processing units may be configured of one processor. As an example where a plurality of processing units are configured of one processor, first, as represented by a computer, such as a client or a server, there is a form in which one processor is configured of a combination of one or more CPUs and software, and the processor functions as a plurality of processing units. Secondly, as represented by system on chip (SoC) or the like, there is a form in which a processor that implements all functions of a system including a plurality of processing units into one integrated circuit (IC) chip is used. In this way, various processing units may be configured using one or more processors among various processors described above as a hardware structure.

In addition, the hardware structure of various processors is, more specifically, an electric circuit (circuitry) in which circuit elements, such as semiconductor elements, are combined.

In the embodiment, although an aspect where the display control program 30 is stored (installed) in the storage unit 22 in advance has been described, the present disclosure is not limited thereto. The display control program 30 may be provided in a form of being recorded in a recording medium, such as a compact disc read only memory (CD-ROM), a digital versatile disc read only memory (DVD-ROM), or a universal serial bus (USB) memory. The display control program 30 may be in a form of being downloaded from an external device through a network.

EXPLANATION OF REFERENCES

What is claimed is:

1. A display control device comprising:
a processor configured to:
perform control for displaying a bar for plotting an inspection result for each inspection item in a subject with one direction of the bar representing a value of the inspection result; and displaying a normal value range and an abnormal value range in the bar with different shaded colors; and
perform control for displaying information representing a predetermined number of inspection results of at least one inspection item of the subject or the same variety as a variety of the subject for a predetermined inspection item along the one direction of the bar with different color or density depending on a frequency of a value being appeared among the predetermined number of inspection results, and displaying a mark representing a last inspection result among the predetermined number of inspection results in the bar.

2. The display control device according to claim 1,
wherein, in a case where the subject is an animal, the variety is an animal variety, and
in a case where the subject is a human, the variety is a human race.

3. The display control device according to claim 1,
wherein, in a case of performing control for displaying information representing the predetermined number of inspection results of the subject, the processor performs control for displaying information representing a previous inspection result before the last inspection result displayed under the control of the processor.

4. The display control device according to claim 1,
wherein, in a case of performing control for displaying information representing the predetermined number of inspection results of the same variety as the variety of the subject, the processor performs control for displaying information representing all inspection results to be acquired from a storage device storing the inspection results of the same variety or a part of last inspection results among all the inspection results.

5. The display control device according to claim 3,
wherein the processor performs control for displaying information representing the predetermined number of inspection results of both of the subject individual and the same variety as the variety of the subject.

6. The display control device according to claim 1,
wherein the processor performs control for displaying information representing one inspection result by one point.

7. The display control device according to claim 6,
wherein, in a case where there are a plurality of inspection results having the same value, the processor performs control for displaying information representing the inspection results having the same value on different axes along the one direction.

8. The display control device according to claim 1,
wherein the processor performs control for displaying information representing the predetermined number of inspection results by a histogram.

9. The display control device according to claim 1,
wherein the processor performs the control by weighting a frequency of a value being appeared among the predetermined number of inspection results using a smaller weight value when the inspection result having the value is older.

10. The display control device according to claim 1,
wherein the processor performs control for displaying information representing the predetermined number of inspection results by changing a display state depending on at least one of the number of inspections results of the predetermined number of inspection results or a proportion of inspection results before a predetermined point of time in the predetermined number of inspection results.

11. The display control device according to claim 10,
wherein the processor performs control for displaying information representing the predetermined number of inspection results by changing color depending on at least one of the number of inspection results of the predetermined number of inspection results or the proportion of inspection results before the predetermined point of time in the predetermined number of inspection results.

12. The display control device according to claim 1,
wherein the processor performs control for displaying the mark by changing color or density between a case where the last inspection result is an abnormal value and a case where the last inspection result is a normal value.

13. The display control device according to claim 1,
wherein the processor is further configured to receive the inspection item selected by an examiner,
wherein the predetermined inspection item is the inspection item received by the processor.

14. The display control device according to claim 1,
wherein the processor is further configured to determine whether or not an inspection result is an abnormal value for each inspection item,
wherein the predetermined inspection item is an inspection item for which an inspection result is determined to be an abnormal value by the processor.

15. The display control device according to claim 1,
wherein the processor is further configured to
receive the inspection item selected by an examiner; and
perform control for displaying a graph representing a history of inspection results including a last inspection result of the subject and a predetermined number of previous inspection results from the last inspection result for the inspection item received by the processor.

16. A display control method comprising:
displaying a bar for plotting an inspection result for each inspection item in a subject with one direction of the bar representing a value of the inspection result, and displaying a normal value range and an abnormal value range in the bar with different shaded colors, and
displaying information representing a predetermined number of inspection results of at least one of the subject or the same variety as a variety of the subject for a predetermined inspection item along the one direction of the bar with different color or density depending on to a frequency of a value being appeared among the predetermined number of inspection results, and displaying a mark representing a last inspection result among the predetermined number of inspection results in the bar.

17. A non-transitory storage medium storing a program causing a computer to execute display control processing, the display control processing comprising:
displaying a bar for plotting an inspection result for each inspection item in a subject with one direction of the bar representing a value of the inspection result, and displaying a normal value range and an abnormal value range in the bar with different shaded colors, and displaying information representing a predetermined number of inspection results of at least one of the subject or the same variety as a variety of the subject for a predetermined inspection item along the one direction of the bar with different color or density depending on a frequency of a value being appeared among the predetermined number of inspection results, and displaying a mark representing a last inspection result among the predetermined number of inspection results in the bar.

18. A display control device comprising:

a processor configured to:

perform control for displaying a bar for plotting an inspection result for each inspection item in a subject with one direction of the bar representing a value of the inspection result;

perform control for displaying information representing a predetermined number of inspection results of at least one of the subject or the same variety as a variety of the subject for a predetermined inspection item along the one direction of the bar by a histogram of the same color and density, wherein the histogram is displayed below the bar and is extended from a bottom side of the bar towards a direction perpendicular to the one direction of the bar; and perform control for displaying a mark representing a last inspection result among the predetermined number of inspection results in the bar.

19. A display control method comprising:

displaying a bar for plotting an inspection result for each inspection item in a subject with one direction of the bar representing a value of the inspection result displaying information representing a predetermined number of inspection results of at least one of the subject or the same variety as a variety of the subject for a predetermined inspection item along the one direction of the bar by a histogram of the same color and density, wherein the histogram is displayed below the bar and is extended from a bottom side of the bar towards a direction perpendicular to the one direction of the bar, and displaying a mark representing a last inspection result among the predetermined number of inspection results in the bar.

20. A non-transitory storage medium storing a program causing a computer to execute display control processing, the display control processing comprising:

displaying a bar for plotting an inspection result for each inspection item in a subject with one direction of the bar representing a value of the inspection result, displaying information representing a predetermined number of inspection results of at least one of the subject or the same variety as a variety of the subject- for a predetermined inspection item along the one direction of the bar by a histogram of the same color and density, wherein the histogram is displayed below the bar and is extended from a bottom side of the bar towards a direction perpendicular to the one direction of the bar, and displaying a mark representing a last inspection result among the predetermined number of inspection results in the bar.

\* \* \* \* \*